United States Patent [19]

Orr et al.

[11] Patent Number: 5,347,843
[45] Date of Patent: Sep. 20, 1994

[54] DIFFERENTIAL PRESSURE FLOWMETER WITH ENHANCED SIGNAL PROCESSING FOR RESPIRATORY FLOW MEASUREMENT

[75] Inventors: Joseph A. Orr; Scott A. Kofoed, both of Salt Lake City, Utah

[73] Assignee: Korr Medical Technologies Inc., Salt Lake City, Utah

[21] Appl. No.: 949,573

[22] Filed: Sep. 23, 1992

[51] Int. Cl.⁵ .............................. G01F 1/36
[52] U.S. Cl. ...................... 73/3; 73/861.52; 73/4 R; 128/725
[58] Field of Search .............. 73/711, 861.42, 861.52, 73/3, 4 R; 128/725; 365/571.01

[56] References Cited

U.S. PATENT DOCUMENTS

| | | |
|---|---|---|
| 3,410,264 | 11/1968 | Frederick . |
| 3,663,833 | 5/1972 | Pao et al. . |
| 3,726,271 | 4/1973 | Mondshine et al. . |
| 3,752,171 | 8/1973 | Ayre . |
| 4,345,463 | 8/1982 | Wilson et al. . |
| 4,476,707 | 10/1984 | Burns et al. ........................ 73/4 |
| 4,581,945 | 4/1986 | Rusz . |
| 5,026,255 | 6/1991 | Carpenter et al. . |
| 5,111,827 | 5/1992 | Rantala ........................ 128/725 X |

OTHER PUBLICATIONS

"Basics of Auto Referencing", Sen Sym, pp. 7-9 through 7-25, undated.
Date brochure, "See Complaince at a Glance", (undated).
Radar, Con, "Pneumotachography", The Perkin Elmer Corporation, California.
Society of Cardiopulmonary Technologies Conference, Oct. 1982.
Saklad, Meyer, et al., "Pneumotachography: A New, Low-Dead space, Humidity-independent Device", Anesthesiology, vol. 5, No. 2, Aug. 1979, pp. 149-153.
Sullivan, William J. et al., "Pneumotachorgraphs: Theory and Clinical Application", Respiratory Care, vol. 29, No. 7, Jul. 1984, pp. 736-739.

Primary Examiner—Herbert Goldstein
Attorney, Agent, or Firm—Trask, Britt & Rossa

[57] ABSTRACT

A pressure differential flowmeter for respiratory flow measurement having enhanced signal processing. The non-linear nature of the signal generated by the differential pressure transducer is accommodated over a wide range of flows via a bank of amplifiers having differing gains, while baseline drift is compensated for by a combined analog and digital auto-referencing technique.

17 Claims, 10 Drawing Sheets

DIFFERENTIAL PRESSURE FLOWMETER WITH ENHANCED SIGNAL PROCESSING FOR RESPIRATORY FLOW MEASUREMENT

BACKGROUND OF THE INVENTION

Field Of the Invention: The present invention relates to respiratory flow measurement, and specifically to improving the performance of differential pressure flowmeters through enhanced signal processing.

State of the Art: Respiratory flow measurement during the administration of anesthesia and in intensive care environments provides valuable information for assessment of pulmonary function and breathing circuit integrity. Many different technologies have been applied to create a flowmeter that meets the requirements of the critical care environment. Among the flow measurement approaches which have been employed are:

1) Differential Pressure—measuring the pressure drop or differential across a resistance to flow.
2) Spinning Vane—counting the revolutions of a vane placed in the flow path.
3) Hot Wire Anemometer—measuring the cooling of a heated wire due to airflow passing around the wire.
4) Ultrasonic Doppler—measuring the frequency shift of an ultrasonic beam as it passes through the flowing gas.
5) Vortex Shedding—counting the number of vortices that are shed as the gas flows past a strut placed in the flow stream.
6) Time of Flight—measuring the arrival time of an impulse of sound or heat created upstream to a sensor placed downstream.

Each of the foregoing approaches has various advantages and disadvantages, and an excellent discussion of most of these aforementioned devices may be found in W. J. Sullivan; G. M. Peters; P. L. Enright, M. D.; "Pneumotachographs: Theory and Clinical Application," *Respiratory Care*, July 1984, Vol. 29-7, pp. 736–49, and in C. Rader, *Pneumotachography*, a report for the Perkin-Elmer Corporation presented at the California Society of Cardiopulmonary Technologists Conference, October 1982.

At the present time, the most commonly employed device for respiratory flow measurement is the differential pressure flowmeter. Because the relationship between flow and the pressure drop across a restriction or other resistance to flow is dependent upon the design of the resistance, many different resistance configurations have been proposed. The goal of all of these configurations is to achieve a linear relationship between flow and pressure differential. It should be noted at this point that the terms "resistance" and "restriction" as applied herein to the physical configuration which produces a pressure drop or differential for use as a flowmeter input signal may be used interchangeably.

In theory, a differential pressure sensor across any resistance to flow constitutes a flowmeter. However, most flow resistances yield a differential pressure signal that is proportional to the square of the flow through the resistance. This "pressure squared" effect leads to a signal that is very small at low flows and is large at high flow rates. This phenomenon results in flowmeters that are either inaccurate at low flows or are incapable of measurements at high flows.

To accurately measure the pressure drop produced from very low flow through a restriction, the signal from the differential pressure transducer sensing the pressure must be amplified greatly to allow accurate reading. However, since the circuitry will not support signal voltages that are greater than its supply voltage, large voltage signals will be clipped off. Thus, the measurement of high flow rates will be limited by the gain of the amplifier circuitry. This limitation is compounded by the pressure squared effect. Traditionally, an optimal single, fixed gain is selected that will allow an acceptable dynamic range of operation for the flowmeter.

To some degree, the pressure squared effect can be compensated for in software of a processing unit associated with the pressure sensor of the flowmeter. If the pressure signal is digitized, the microprocessor can compensate for any non-linear relationship between differential pressure and flow. However, this compensation is limited by the resolution with which the signal is digitized. Currently, high resolution analog-to-digital converters are cost-prohibitive for use with differential pressure flowmeters. With limited analog-to-digital converter resolution, a one-bit change in the digitized pressure level may correspond to large flow differences at low flows, leading to poor accuracy at low flow.

In some prior art differential pressure flowmeters (commonly termed pneumotachs) the flow restriction has been designed to create a linear relationship between flow and differential pressure. Such designs include the Fleisch pneumotach in which the restriction is comprised of many small tubes or a fine screen, ensuring laminar flow and a linear response to flow. Another physical configuration is a flow restriction having an orifice variable in relation to the flow. This arrangement has the effect of creating a high resistance at low flows and a low resistance at high flows. Among other disadvantages, the Fleisch pneumotach susceptible to performance impairment from moisture and mucous, and the variable orifice flowmeter is subject to material fatigue and manufacturing variabilities.

One problem with pressure sensors employed in differential pressure pneumotachs is baseline drift. One technique, known as auto-referencing is used to compensate for baseline drift. The topic is discussed generally and with respect to flow measurement in "Basics of Auto-Referencing," application note SSAN-2, SENSYM Catalog, 1991. In differential pressure pneumotach auto-referencing, valves are used to create a direct pneumatic connection between the two pressure ports of the differential pressure transducer. This shunt or bypass connection corresponds to zero flow through the flow resistance. The pressure measurement at zero flow is sorted and subtracted from future measurements to compensate for baseline drift. This subtraction is normally done digitally in a computer program, but might also be performed using an analog circuit. However, the digital subtraction technique currently requires either a linear flowmeter or high resolution analog to digital conversion of the non-linear pressure signal.

SUMMARY OF THE INVENTION

The present invention uses a new approach to overcome the problems of the pressure squared effect and baseline drift in differential pressure flowmeters. The invention uses a circuit in which the differential pressure signal is amplified using a bank of multiple amplifiers arranged to yield increasing gain levels or stages, for example 1, 10, 100 and 1000. The output of each amplifier is input via a multiplexer into an analog-to-digital converter. One amplifier channel is designated to sample the signal at very low flows, the next at higher flows and so on. The appropriate channel signal, dependant upon flowrate, is selected and employed as an output signal and converted to an indication of flowrate.

To compensate for baseline drift of the pressure sensor, the invention uses the auto-referencing technique. However, rather than only subtracting the baseline flow digitally as in the prior art, the system of the present invention subtracts the baseline signal from the differential pressure signal first in an analog circuit and also digitally for each of the gain channels. The system uses a digital-to-analog converter and a differential amplifier to subtract the baseline offset in analog. Analog subtraction of the baseline signal allows amplification to higher levels (such as $\times 100$ and $\times 1000$) without clipping the signal. Without such compensation, any drift in the baseline signal would cause these higher-gain amplifiers to saturate and would impede measurement at low flow-rates. The digital values of each of the amplifier outputs during auto-referencing (baseline signal) is also stored and subtracted digitally from each of the signals generated during flow measurement. This digital subtraction is necessary because of the limited resolution of the digital-to-analog converter and to set the value about zero for inspired and expired flow.

The flowmeter system of the present invention is comprised of a flow restriction in a respiration tube or conduit, an airway pressure sensor, a differential pressure sensor in communication with the tube across the flow restriction, auto-referencing valves and a bypass tube to communicate the pressure ports of the differential pressure sensor, a digital-to-analog converter, a multi-channel analog-to-digital converter, a subtracting amplifier, a bank of amplifiers providing progressively larger gains and a microprocessor. Pressure takeoff tubes are connected to the respiration tube or conduit on either side of the flow restriction and to the auto-referencing valves. In a first "normally open" position or mode these valves permit communication via the tubes between the interior of the conduit on each side of the flow restriction and a respective side of the differential pressure sensor. In a second "normally closed" position or mode these valves close off communication to the conduit and connect the two ports of the pressure sensor to each other via the bypass tube to simulate a zero flow situation for sensor baseline compensation. This output signal is digitally stored in the microprocessor and is also input to the subtracting amplifier via the digital-to-analog converter for baseline offset purposes. The output signal from the differential pressure sensor is also input to the aforementioned subtracting amplifier, which has a gain of approximately one. The output of the subtracting amplifier is fed into a bank of four progressively higher-gain amplifiers preferably configured in parallel, although a series configuration is also contemplated and illustrated herein. The amplifiers in the bank of the preferred embodiment have gains of 1, 10, 100 and 1000 respectively (these gains may be optimized for a given restriction and flow rate range). Each of these amplifiers is connected via a multiplexer to the analog-to-digital converter; the amplifier channels are input to the multiplexer, then the multiplexer output is single input to the analog-to-digital converter. The signal values from all of the channels of the analog-to-digital converter are collected simultaneously and the previously digitally stored baseline or offset value subtracted from each. The correct channel from which flow can be measured is selected by the microprocessor using one of several selection routines via appropriate software, and a look-up table, a piece-wise linear function or an equation of state is used to calculate flow from the measured differential pressure in combination with the pressure sensed by the airway pressure sensor which is also digitized.

DETAILED DESCRIPTION OF THE PREFERRED EMBODIMENT

Figure 1:
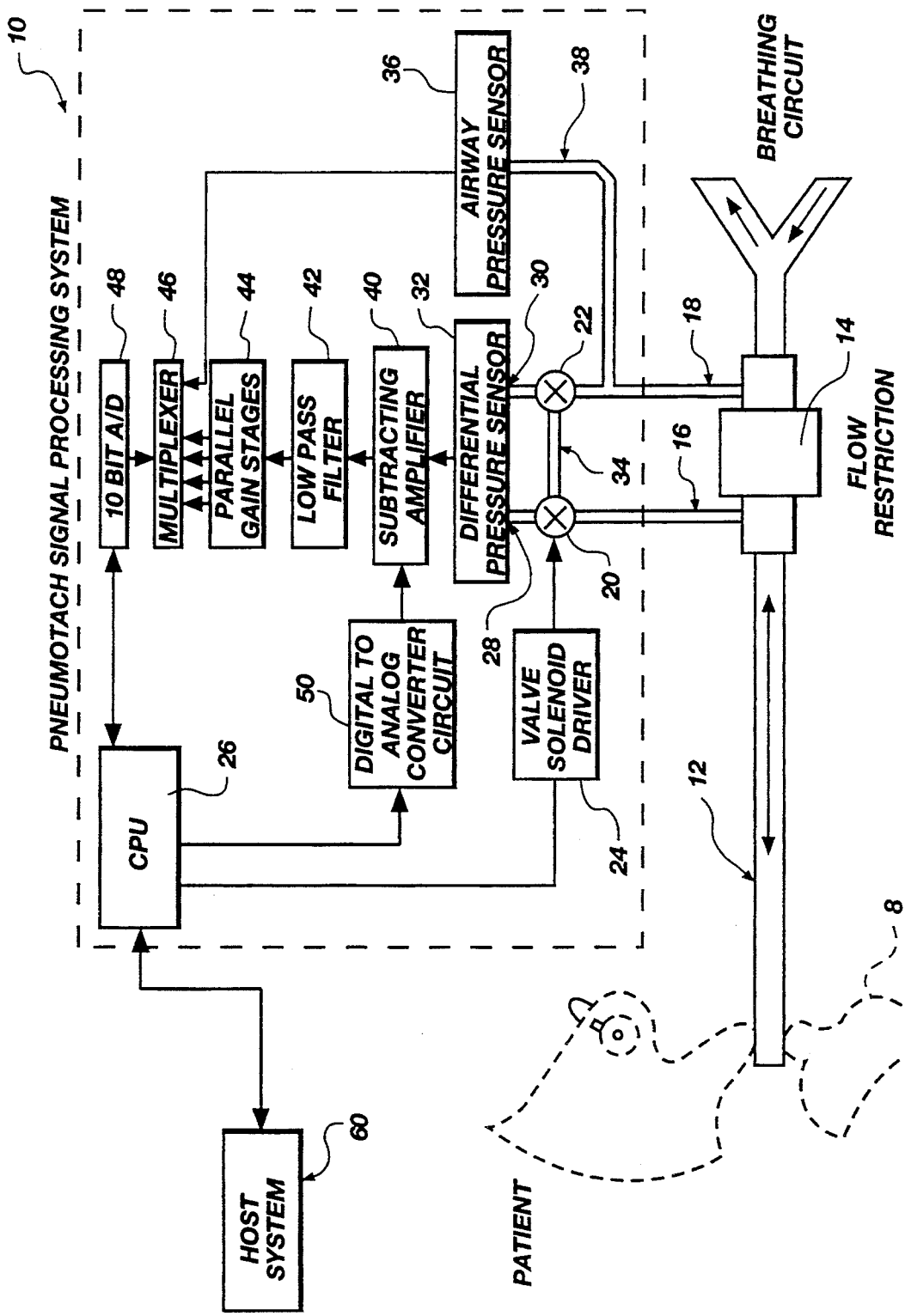
FIG. 1 of the drawings is a schematic of an apparatus for respiratory flow measurement including a flow restriction, a differential pressure sensor and a signal processing system, all according to the present invention.

FIG. 1 of the drawings schematically depicts the differential pressure flowmeter of the present invention, with a patient 8 breathing through a respiration tube 12 having a flow restriction 14 therein. In general terms, the present invention may be said to comprise signal processing system 10, respiration tube 12 and flow restriction 14. Flow restriction 14 may take any form known in the art, such as Datex D-lite sensor, offered by Datex Instrumentarium Corp., Helsinki, Finland. Alternatively, and preferably, the flow restriction may take the form shown in FIGS. 5 or 6 of the drawings, and hereinafter described. It should be understood, however, that any suitable flow restriction may be employed with the present invention. Referring again to FIG. 1, first and second pressure takeoff tubes 16 and 18, one on each side of flow restriction 14, extend respectively to first and second three-way valves 20 and 22 driven by solenoid driver 24 in response to commands from central processing unit (CPU) 26. Valves 20 and 22 are configured to provide communication in a first mode or position from breathing tube 12 through first and second takeoff tubes to pressure ports 28 and 30 of differential pressure sensor 32, and in a second mode or position between ports 28 and 30 through shunt or bypass tube 34 in isolation from respiration tube 12 for auto-referencing, which will be explained hereinafter in detail. It should be noted that an airway pressure sensor 36 is in communication with respiration tube 12 through auxiliary pressure takeoff tube 38 which connects to second pressure takeoff tube 18 between valve 22 and respiration tube 12. Differential pressure sensor 32 provides an analog signal to subtracting amplifier 40, which in turn provides a signal to a plurality of amplifiers providing different parallel gain stages 44 through low pass filter 42. The signals from each of the gain stages 44, in conjunction with a signal from airway pressure sensor 36, are received by multiplexer 46 and forwarded to ten bit analog-to-digital convertor 48 under control of CPU 26. Digital-to-analog convertor circuit 50 is also included in the signal processing system 10 of the present invention. CPU 26 communicates the signal processing system 10 of the present invention with a host system 60 such as a PC with readout, display and/or alarm means associated therewith.

Figure 2:
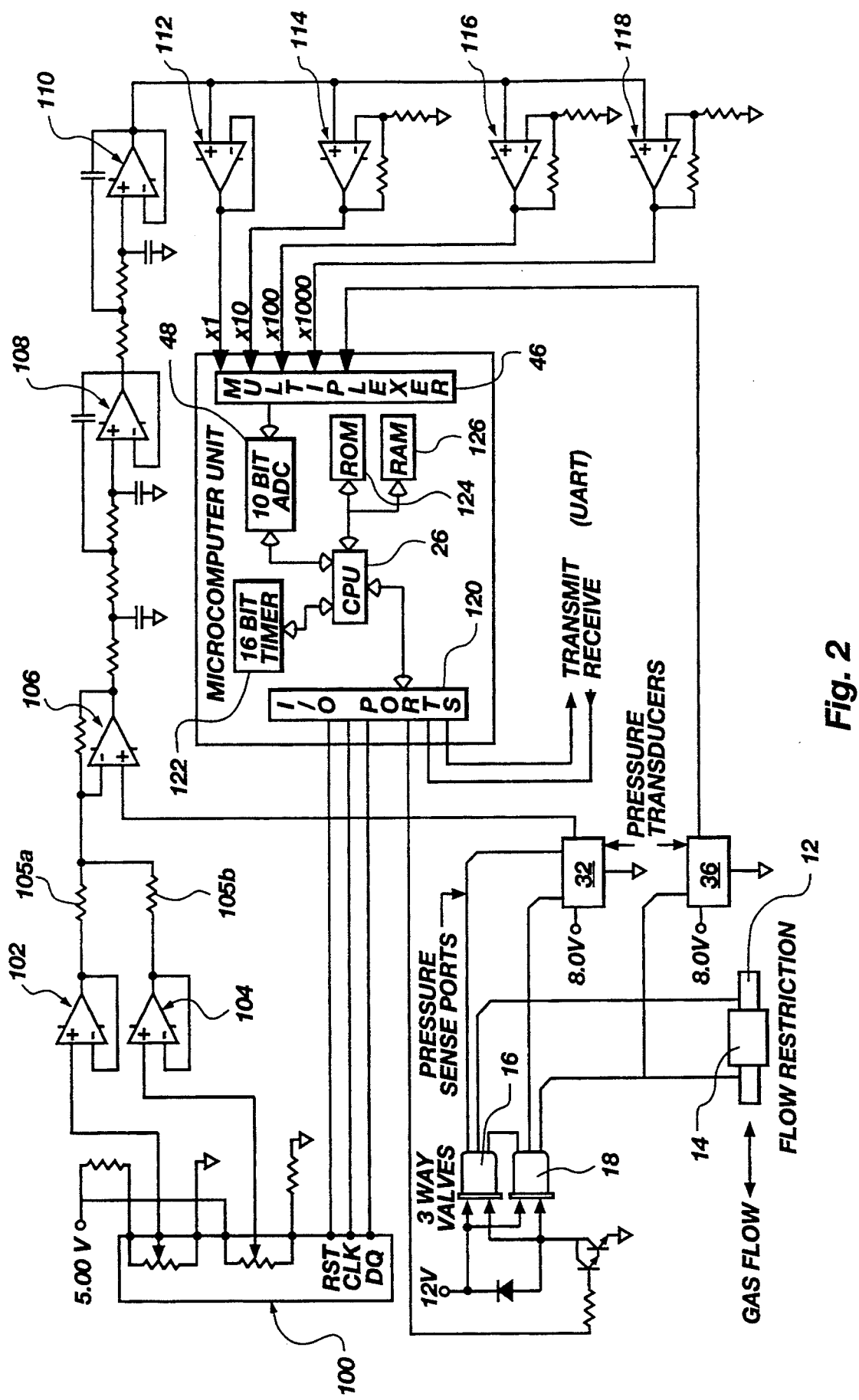
FIG. 2 is a gas flow and electronic circuit schematic for a preferred embodiment of the invention, depicting a bank of amplifiers for parallel gain realization.

A gas flow and circuit schematic for a differential pressure flowmeter with parallel gain realization according to the present invention is depicted in FIG. 2 of the drawings. Elements described with respect to FIG. 1 are identified in FIG. 2 by the same reference numerals. Additional elements of signal processing system 10 depicted in FIG. 2 include digital potentiometer 100 and operational amplifiers (op-amps) 102 and 104, which together with resistors 105a and 105b comprise digital-to-analog converter 50 (see FIG. 1). Op-amp 106 is a differential amplifier which is also referenced as subtracting amplifier 40 in FIG. 1. Op-amps 108 and 110 comprise a 5th order Butterworth low pass filter, referenced as 42 in FIG. 1. Op-amps 112, 114, 116 and 118 provide the parallel gain stages (X1, X10, X100 and X1000, respectively) referenced collectively as 44 in FIG. 1. Input/output ports 120 link CPU 26 to digital-to-analog converter 50 via digital potentiometer 100, as well as to the host system 60 via the depicted transmit and receive circuit, which preferably comprises a UART. Sixteen bit timer 122, ROM 124 and RAM 126 complete the major components of signal processing system 10. Preferred system components include a Dallas Semiconductor digital potentiometer #DS 1267 (digital potentiometer 100), a Honeywell #163PC01D36 MICROSWITCH differential pressure transducer (differential pressure sensor 32), and an Hitachi H8/532 microcomputer unit including the CPU 26, sixteen bit timer 122, multiplexer 46, ROM 124, RAM 126, ten bit analog-to-digital converter 48 and input-/output ports 120, as shown in FIG. 2.

Figure 4A:
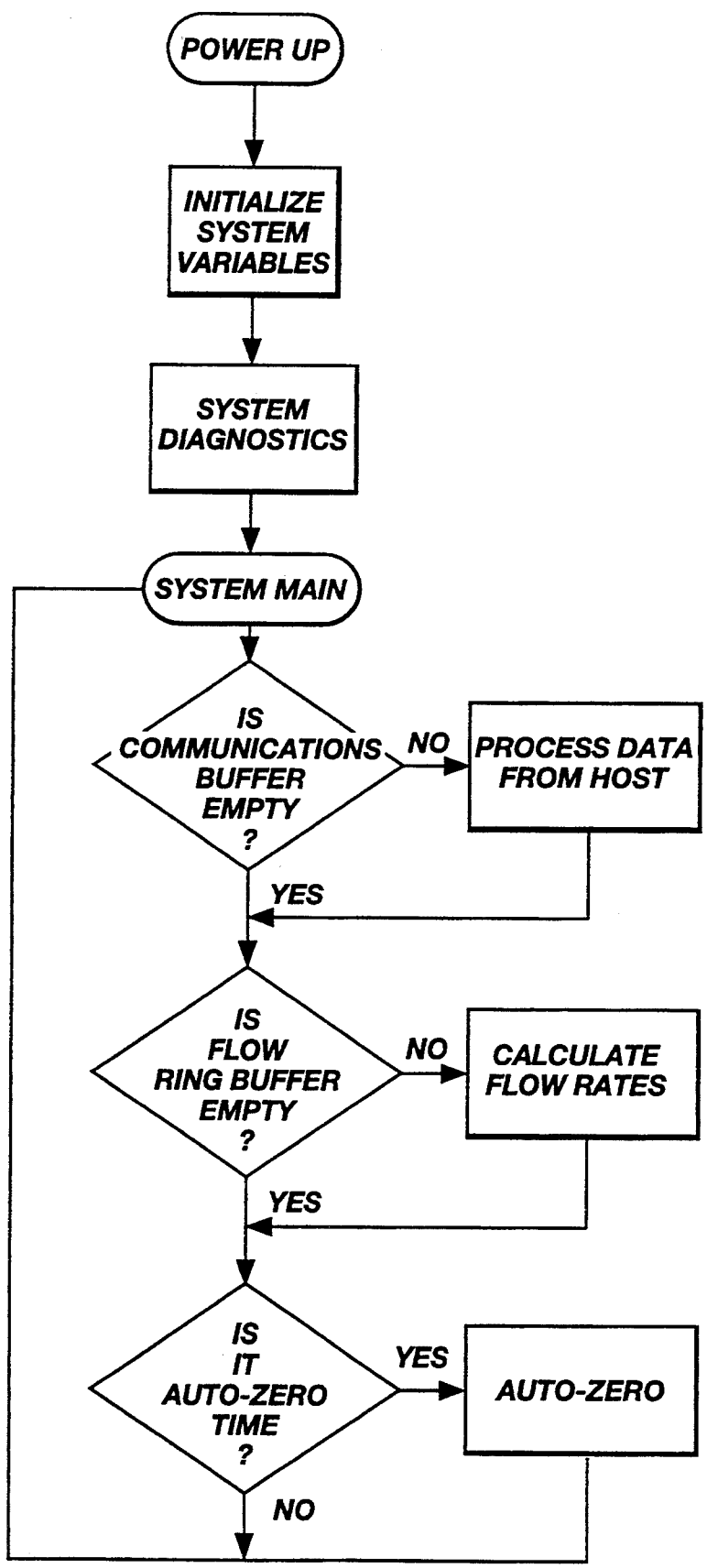
FIGS. 4A–4F comprise flow charts of the operation of the signal processing system of the present invention.
Figure 4B:
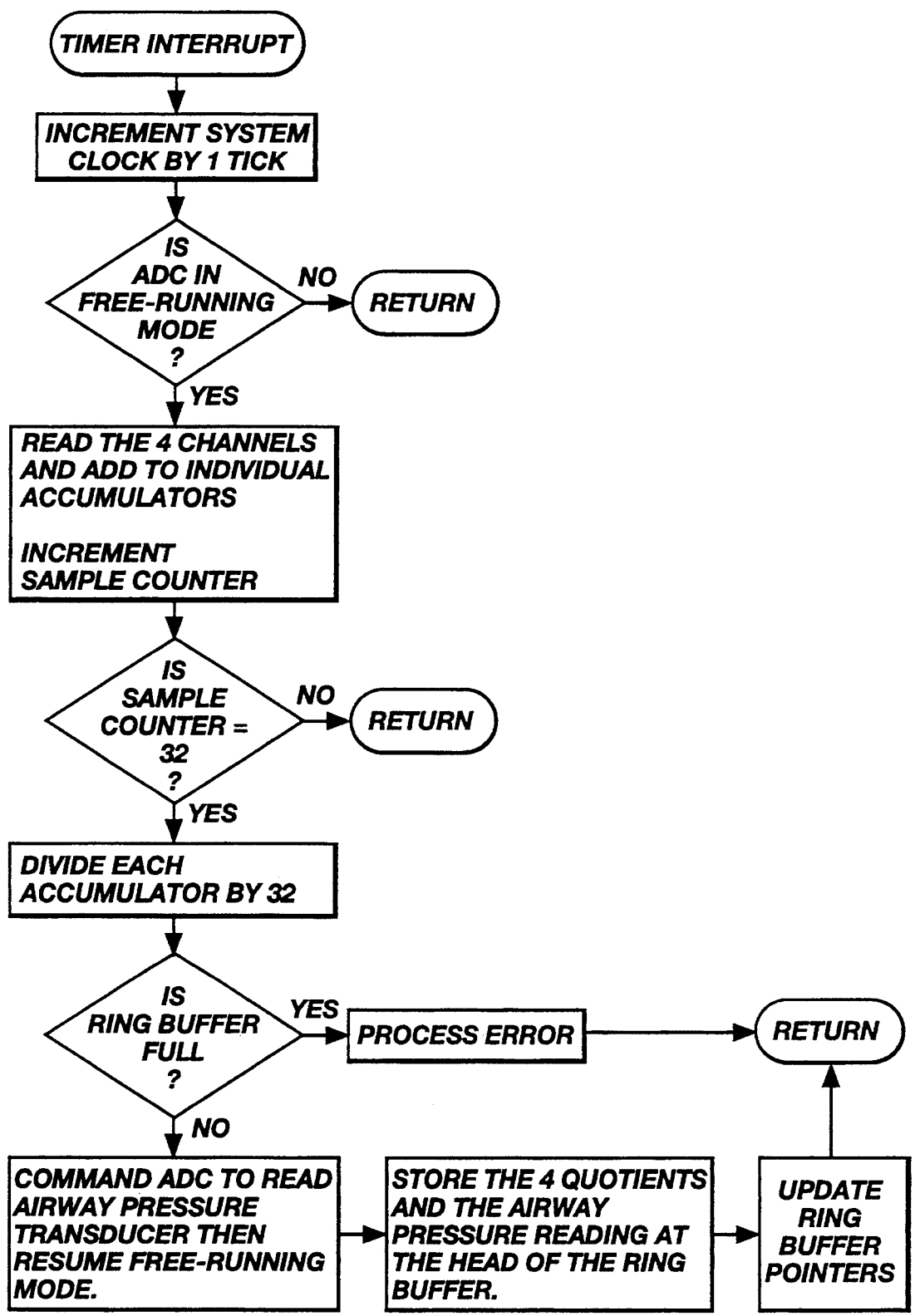
Figure 4C:
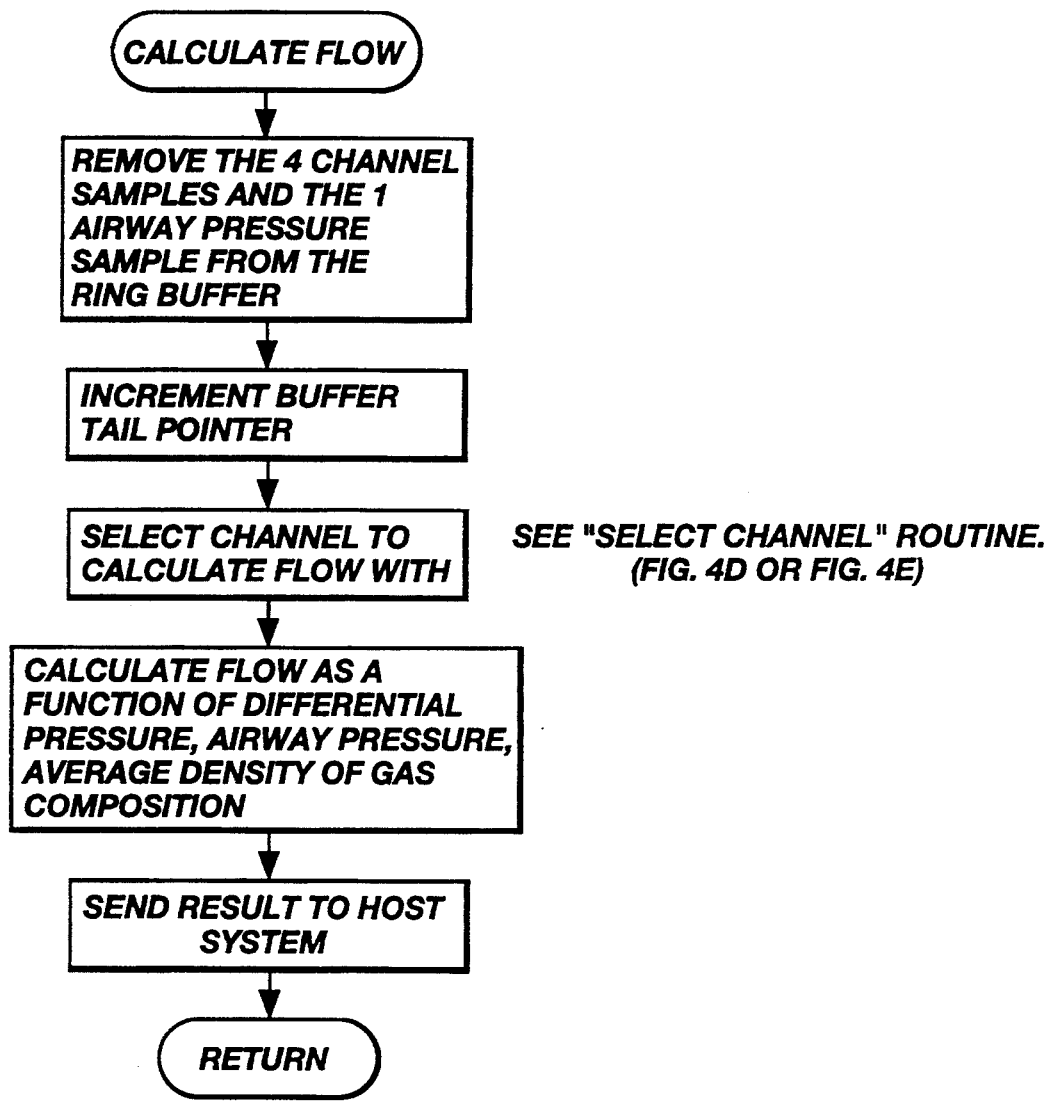
Figure 4D:
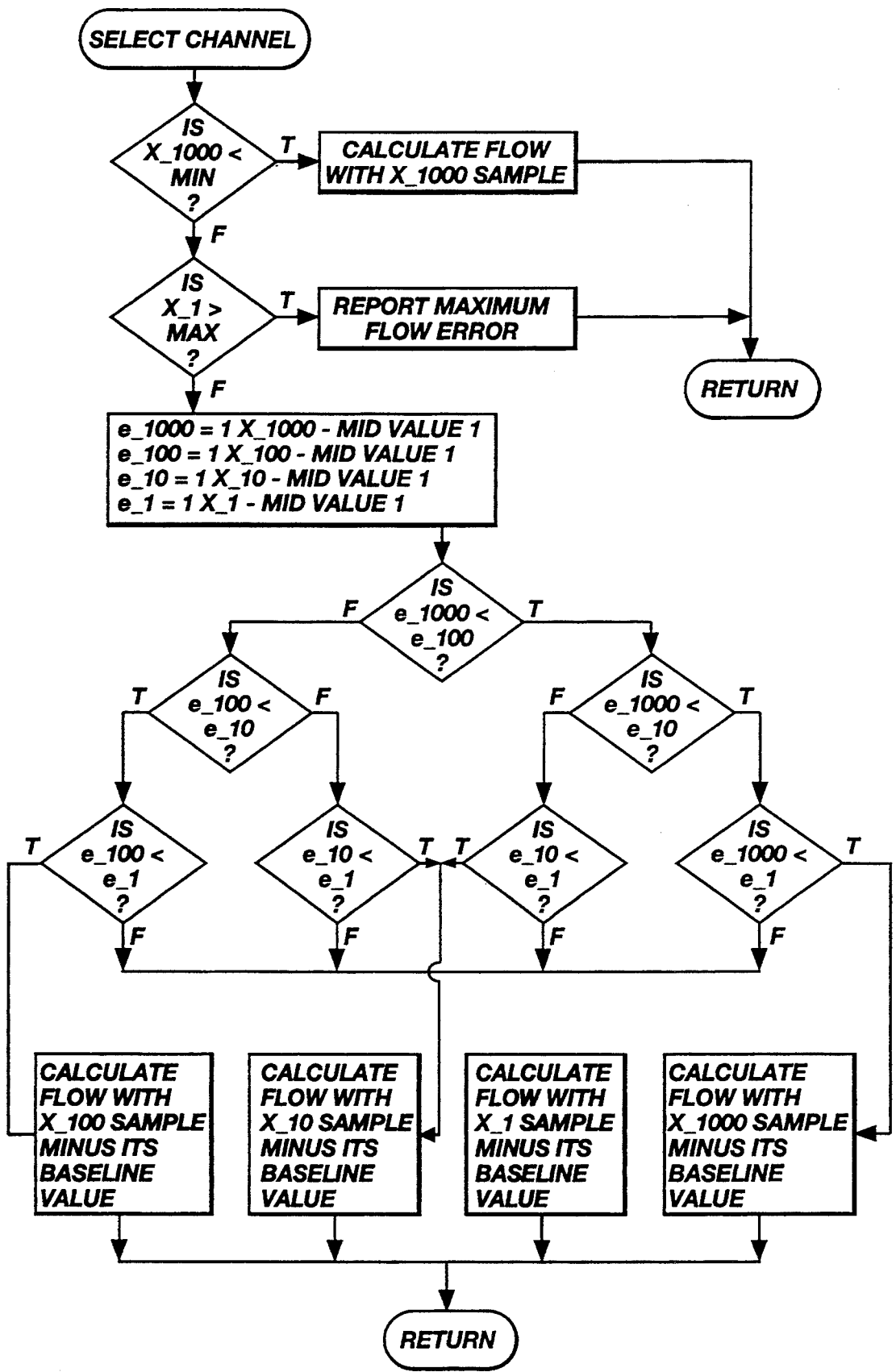
Figure 4E:
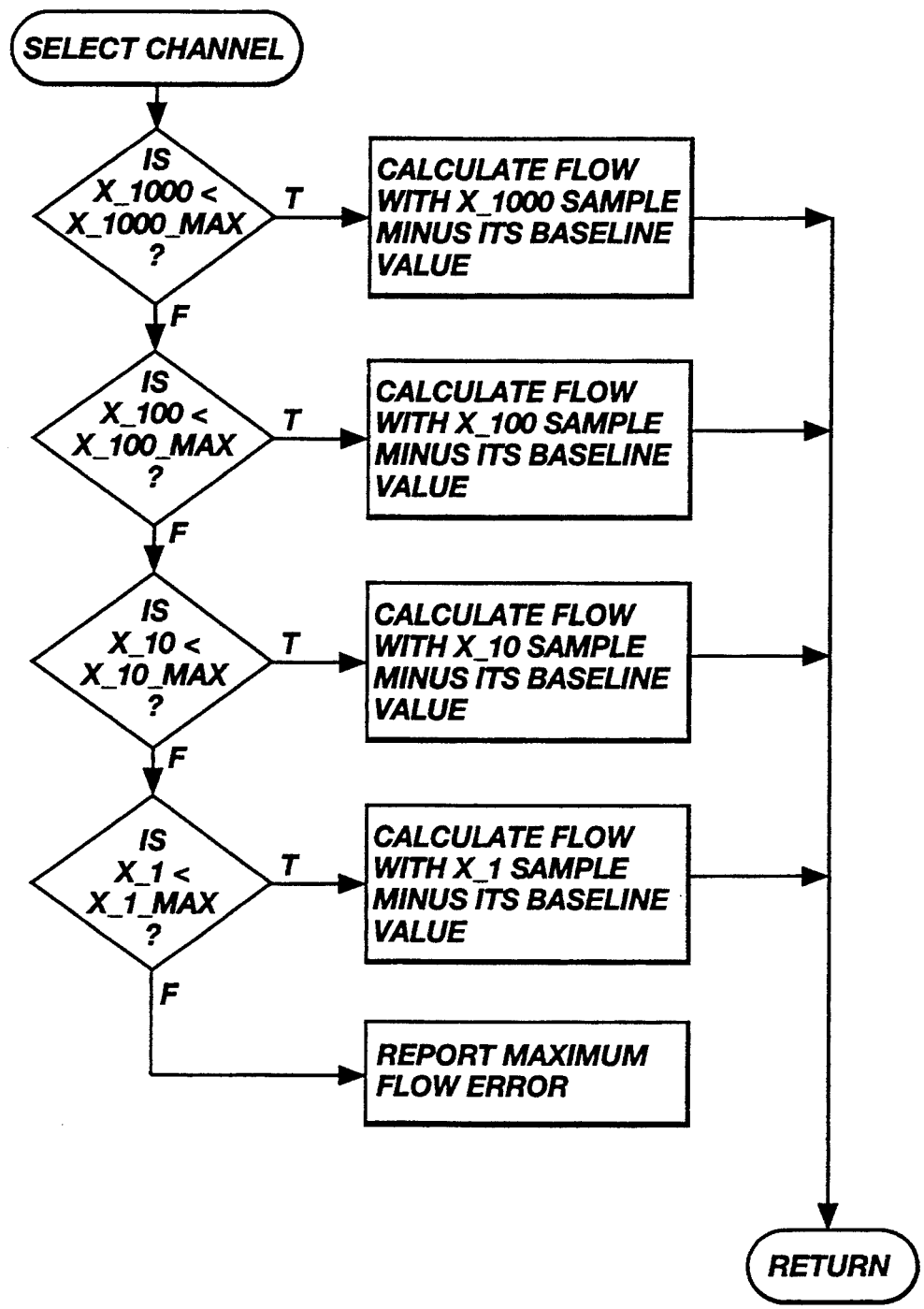
Figure 4F:
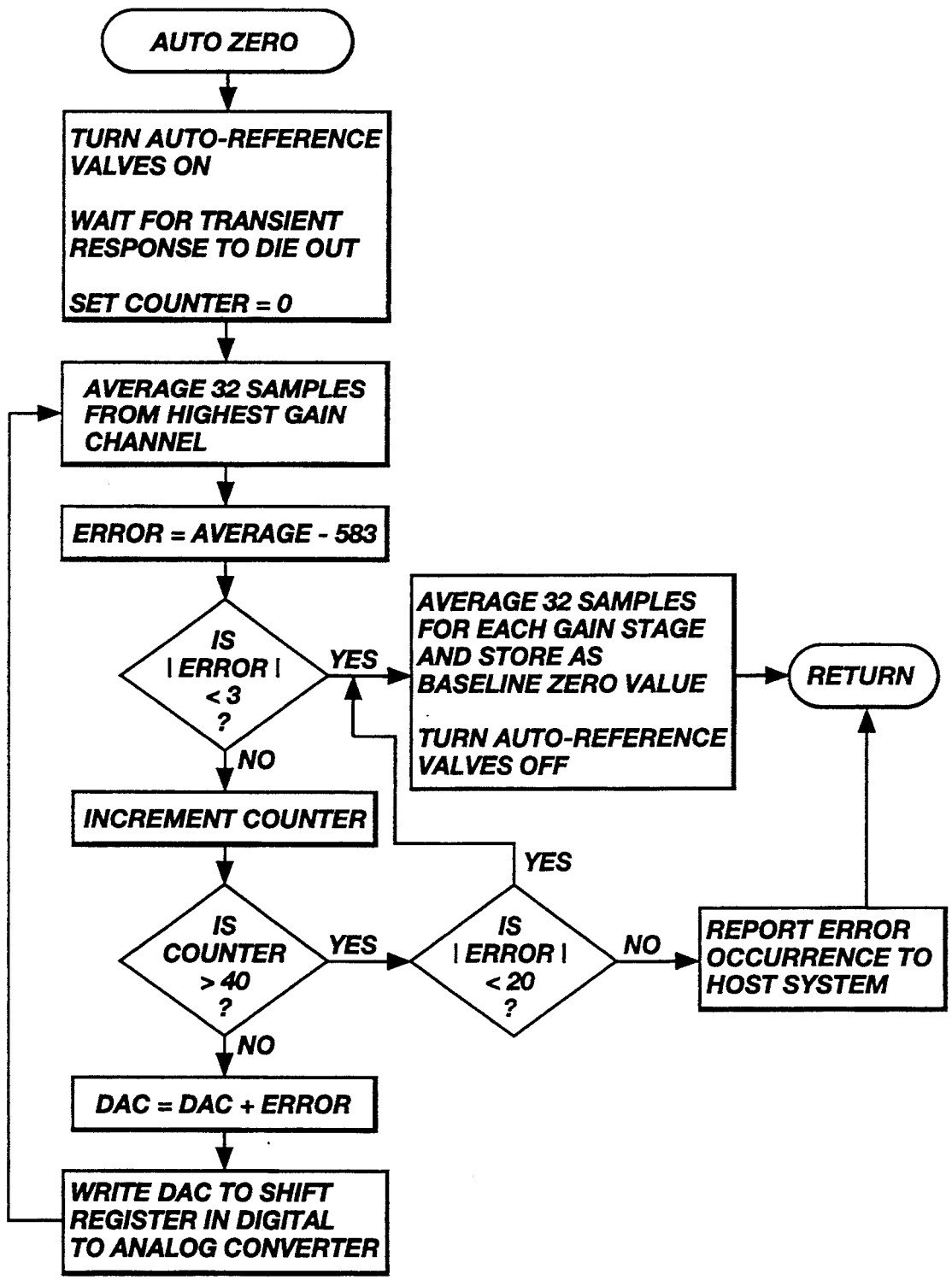

The operation of the differential pressure flowmeter of the present invention is schematically depicted in the flow charts of FIGS. 4A-4F. Specifically, FIG. 4A depicts the basic system operating routine including host/system communications data processing, flow rate calculations and auto-zeroing of the system. FIG. 4B depicts the timer-interrupt triggered sampling and processing sequence of the present invention, by which data for flow calculations reaches the ring buffer referenced in FIG. 4A. FIG. 4C depicts the flow rate calculation routine as generally referenced in FIG. 4A. The "SELECT CHANNEL" subroutine employed in the "CALCULATE FLOW" routine of FIG. 4C may be that shown in FIG. 4D if it is desired to select a channel output signal that is closest to mid-span, or that of FIG. 4E if it is desired to select a channel output signal that is closest to full scale without saturation. FIG. 4F depicts the auto-zeroing routine employed in the system as generally referenced at the bottom of FIG. 4A.

By way of further explanation of the operation of the present invention as depicted in FIGS. 1 and 2 of the drawings, patient 8 is breathing through respiration tube 12 having flow restriction 14 disposed therein. Per FIG. 4A, signal processing system 10 is powered up, system variables initialized, and internal system diagnostics run. The system 10 then addresses the communications buffer for communication from host system 60, thereafter addresses the memory (flow ring buffer) for data for flow rate calculation (there being none initially) and advances to the auto-zero sequence of FIG. 4F.

The auto-zero or auto-referencing cycle is carried out periodically during system operation, and is initiated by the CPU 26 causing valve solenoid driver 24 to energize and switch valves 20 and 22 from their first mode to their second mode, wherein pressure ports 28 and 30 of differential pressure sensor 32 are in communication through shunt bypass tube 34 in isolation from respiration tube 12. The output signal values of amplifiers 112-118 for a number (typically thirty-two) of baseline pressure samples are measured, digitized, averaged and stored for each amplifier channel in the microcomputer unit, and the analog offset (baseline adjustment) of subtracting amplifier 40 (also depicted in FIG. 2 as op-amp 106) is updated from CPU 26 through digital-to-analog converter circuit 50 until the most sensitive (highest gain) channel (from amplifier 118) of the amplifier bank (parallel gain stages) 44 is centered in its range, typically about 3.5 volts. System 10 then stores the outputs of all the amplifier channels in RAM 126. Valves 20 and 22 are then switched back to their first mode by CPU 26 by de-energizing valve solenoid driver 24, and differential pressure across flow restriction 14 and airway pressure is then monitored so that gas flow rates may be calculated.

During normal measuring operation (see FIG. 4B), system 10 samples each of the four channels of analog-to-digital converter 48 every 500 microseconds, triggered by an interrupt from timer 122. Analog-to-digital converter 48 can operate in a free-running mode, continuously sampling amplifiers 112-118. At any given time while in such mode, the last conversion results for the four amplifier channels are available from the analog-to-digital converter. As with the auto-zero routine, thirty-two samples of each amplifier output are digitized and summed into an accumulator, one sample per channel per interrupt. When thirty-two samples have been added in each accumulator, software divides the sum by thirty-two, and places the resulting averages and a sample or reading from airway pressure sensor 36 into a ring buffer memory. The system sequence and timing permits flow rates to be calculated and reported every 16 milliseconds.

The main software loop periodically removes the four averaged amplifier signals and the airway pressure samples from the ring buffer (see FIG. 4C), and for each gain stage (X1, X10, X100 and X1000) the digital value recorded during the last (most recent) auto-referencing cycle is subtracted to more accurately compensate for baseline drift. Since at this point there are four averaged, compensated signal samples, one from each gain stage, a suitable algorithm is used to select the appropriate channel to be processed to arrive at the gas flow rate. FIGS. 4D and 4E, as previously noted, offer two alternatives for channel selection, one being for midspan output, the other and preferred alternative targeting a full scale but unsaturated output selection. Once the appropriate channel output is selected, a look-up table, piece-wise linear function or equation of state, all as known in the art, may be used to convert the differential pressure signal in conjunction with the airway pressure signal to a flow rate.

Figure 3:
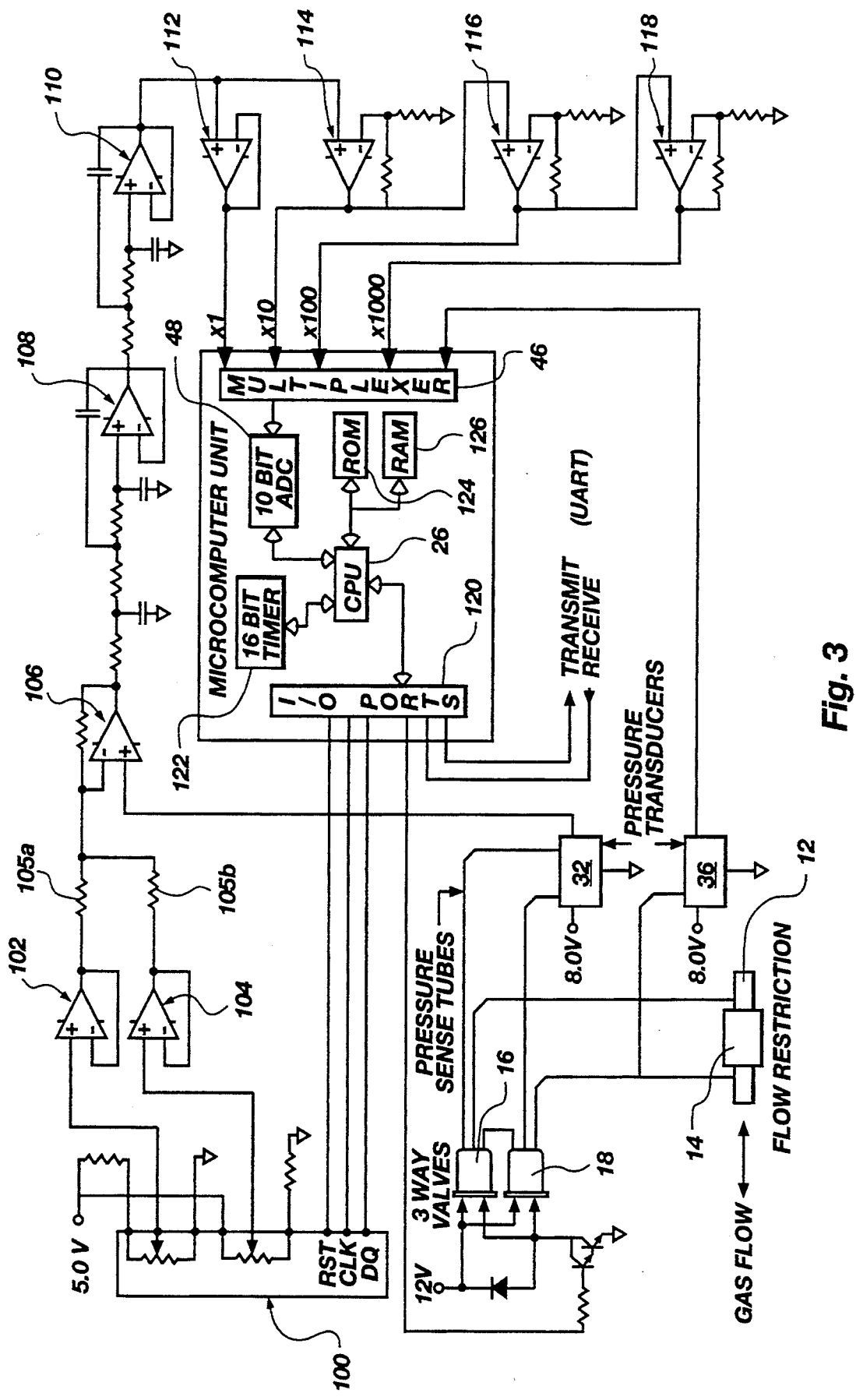
FIG. 3 is a gas flow and electronic circuit schematic for an alternative embodiment of the invention, depicting a bank of amplifiers for series gain realization.

FIG. 3 of the drawings depicts an alternative schematic wherein amplifiers 112, 114, 116 and 118 are deployed in series, with the output of amplifier 114 being input to amplifier 116, and the output of amplifier 116 input to amplifier 118. But for the foregoing differences, the circuits of FIGS. 2 and 3 are identical. The operating sequence described above and depicted in FIGS.

4A–4F with respect to FIG. 2 is equally applicable to FIG. 3.

Figures 5A, 5B:
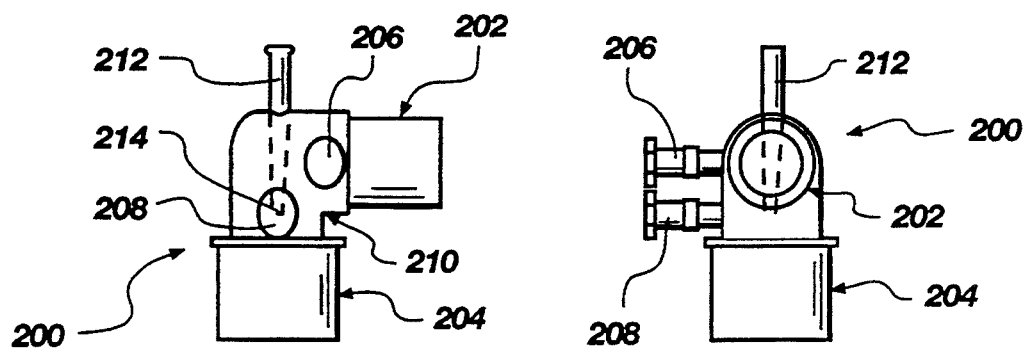
FIG. 5A and 5B comprise side and front elevations of a first embodiment of a flow sensor which may be employed with the present invention.

Referring to FIG. 5 of the drawings, an elbow 200 having legs 202 and 204, such component as is part of a SafeTrak ™ Breathing Circuit, code #8624, from Kendall Healthcare Products Co., Mansfield, MA, has been modified for use as a preferred flow restriction 14 in accordance with the present invention. Pressure sense ports 206 and 208 have been extended through and from the wall of elbow 200 on either side of the elbow angle 210 for connection to differential pressure sensor 32 via tubes 16 and 18. Gas sample tube 212 having port 214 within elbow 200 is a standard component of the elbow. In this configuration of flow restriction 14, the elbow itself and the gas sample tube 212 provide the flow restriction to cause the pressure differential.

Figure 6:
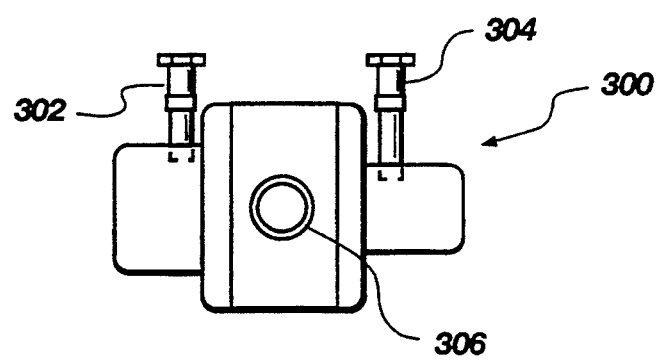
FIG. 6 is a side elevation of a second embodiment of a flow sensor which may be employed with the present invention.

FIG. 6 illustrates a modified $CO_2$ cuvette 300, such as a NOVAMETRIX Medical Systems, Inc. (Wallingsford, CT) part #4989. Cuvette 300 has been modified by the addition of pressure sense ports 302 and 304 on either side of indentation 306, which provides the required flow restriction and is already present in the cuvette for placement of the $CO_2$ detector over the cuvette.

Thus, it will be obvious to those skilled in the art that a novel and unobvious differential pressure flowmeter with enhanced signal processing has been invented. Many additions, deletions and modifications to the preferred and alternative embodiment as disclosed herein will be readily apparent to those of ordinary skill in the art and may be effectuated without departing from the scope of the claimed invention. For example, more or fewer than four gain stages may be employed in the invention, the gain values and their relative magnitudes may differ from those described herein and other flow restrictions may be employed, and the number of pressure samples and the sampling period as well as the frequency of auto-referencing may be varied.

What is claimed is:

1. A differential pressure flowmeter for measurement of respiratory gas flow, comprising:
    a conduit for conducting said respiratory gas flow having a flow restriction therein and first and second apertures through the wall thereof on opposite sides of said flow restriction;
    a pressure sensor for generating a signal responsive to pressure in said conduit;
    a differential pressure sensor having first and second pressure ports for generating a signal responsive to differential pressure across said restriction;
    a first pressure passage extending between said first conduit aperture and said first pressure port;
    a second pressure passage extending between said second conduit aperture and said second pressure port;
    a third pressure passage;
    first and second valves respectively associated with said first and second pressure passages and in communication with said third pressure passage for selectively communicating said first and second pressure ports of said differential pressure sensor with said first and second apertures in a first valve mode and said first and second pressure ports with each other in isolation from said conduit in a second valve mode;
    a subtracting amplifier for receiving said signal from said differential pressure sensor and for compensating said signal by a baseline signal generated by said differential pressure sensor when said first and second pressure ports are communicated in isolation from said conduit;
    a plurality of amplifiers having differing gain stages for receiving said compensated signal from said subtracting amplifier and amplifying said compensated signal;
    an analog-to-digital converter for receiving an amplified signal from each of said plurality of amplifiers and digitizing such amplified signals and for receiving and digitizing said pressure sensor signal; and
    microprocessor means for selecting one of said digitized amplified signals and converting said selected digitized amplified signal and said digitized pressure sensor signal to a flow rate of said respiratory gas.

2. The apparatus of claim 1, further including a digital-to-analog converter, and wherein said microprocessor is adapted to change said first and second valves from said first valve mode to said second valve mode, said microprocessor means being further adapted to provide said baseline signal to said subtracting amplifier for said signal compensation via said digital-to-analog converter for subtraction from said differential pressure transducer signal during flow measurement.

3. The apparatus of claim 2, wherein said baseline signal provided to said subtracting amplifier is selected by said microprocessor means from baseline signals a plurality of baseline signals as amplified by said plurality of amplifiers so as to center the highest possible gain channel of said plurality of amplifiers within its range.

4. The apparatus of claim 1, further including:
    timing means for causing said analog-to-digital converter to periodically select pressure sample signals of said respiratory gas flow from each of said plurality of amplifiers and said pressure sensor;
    accumulator means for summing a plurality of said signals for each gain stage corresponding to said periodic samples, said microprocessor adapted to average said summed signals by dividing same by the number of periods sampled;
    memory means for storing said averaged signals and said pressure sensor; and
    said microprocessor means being further adapted to subtract said baseline signal from said averaged signal for each gain stage and to select the appropriate resulting signal for conversion with said pressure sensor signal to a flow rate of said respiratory gas flow.

5. The apparatus of claim 4, wherein said microprocessor is adapted to select said resulting signal being closest to its mid-span value.

6. The apparatus of claim 4, wherein said microprocessor is adapted to select said resulting signal being closest to full scale value without being saturated.

7. The apparatus of claim 1, wherein said plurality of amplifiers are arranged in parallel.

8. The apparatus of claim 1, wherein said plurality of amplifiers are arranged in series.

9. The apparatus of claim 1, wherein said flow restriction comprises an elbow.

10. A differential pressure flowmeter for measurement of respiratory gas flow, comprising:
    pressure sampling means including a conduit with a flow restriction, a differential pressure sensor for generating a signal responsive to differential pressure across said flow restriction, and a pressure sensor for generating a signal responsive to pressure in said conduit;

auto-referencing means for providing a baseline signal from said differential pressure sensor under no-flow conditions;

signal subtraction means for compensating signals from said differential pressure during flow of said respiratory gas with said baseline signal;

a plurality of amplifier means of differing gains for receiving said compensated signals and generating a plurality of amplified signals;

means for digitizing said amplified signals and said pressure sensor signal selecting one of said digitized, amplified signals and converting same with said digitized pressure sensor signal to a flow rate of said respiratory gas.

11. The apparatus of claim 10, further including means for summing and averaging a plurality of amplified signals from each of said plurality of differing gain amplifiers for selection by said means for selecting of one of said plurality of averaged amplified signals.

12. The apparatus of claim 10, further including timing means for causing said means for digitizing to periodically read signals from each of said plurality of differing gain amplifiers and said pressure sensor.

13. The apparatus of claim 10, further including means for subtracting said baseline signal from each of said digitized, amplified signals prior to conversion of the lathe to said flow rate.

14. The apparatus of claim 10, wherein said means for selecting one of said digitized, amplified signals is adapted to select the signal closest to its mid-span value.

15. The apparatus of claim 10, wherein said means for selecting one of said digitized, amplified signals is adapted to select the signal closest to full scale without being saturated.

16. The apparatus of claim 10, wherein said plurality of amplifiers are arranged in parallel.

17. The apparatus of claim 10, wherein said plurality of amplifiers are arranged in series.

* * * * *